US00PP09534P

United States Patent [19]

Trees

[11] Patent Number: Plant 9,534

[45] Date of Patent: Apr. 30, 1996

[54] GERANIUM PLANT NAMED 'BFP-825 SALMON ROSE'

[75] Inventor: Scott C. Trees, Arroyo Grande, Calif.

[73] Assignee: Geo. J. Ball, Inc., West Chicago, Ill.

[21] Appl. No.: 431,722

[22] Filed: May 1, 1995

[51] Int. Cl.[6] ..... A01H 5/00

[52] U.S. Cl. ..... Plt./87.12

[58] Field of Search ..... Plt./87.12

*Primary Examiner*—James R. Feyrer

*Attorney, Agent, or Firm*—Burns, Doane, Swecker & Mathis

[57] ABSTRACT

The new and distinct *Pelargonium×hortorum* cultivar named 'BFP-825 Salmon Rose' is provided. This new Zonal Geranium was the result of a controlled breeding program wherein a plant designated G4111-4 (non-patented in the United States) was pollinated by the 'Laura' cultivar (U.S. Plant Pat. No. 7,087). The new cultivar forms attractive semi-double light rose florets. Medium green foliage with zonation is well retained during shipment. The growth habit is medium self-branching and does not require the use of a growth regulator.

1 Drawing Sheet

SUMMARY OF THE INVENTION

The present invention comprises a new and distinct Geranium cultivar, botanically known as *Pelargonium×hortorum* Bailey, and hereinafter is referred to by the cultivar name 'BFP-825 Salmon Rose'.

The new cultivar is a product of a planned breeding program which had the objective of the creation of a Geranium cultivar that exhibts uniform flowers, medium green foliage, a medium self-branching growth habit that requires no growth regulator, a propensity for rapid rooting, and stable foliage coloration during shipment.

The breeding program that resulted in the production of the new cultivar of the present invention was carried out in a controlled environment during 1992 at Arroyo Grande, Calif., U.S.A. The female parent (i.e., seed parent) was a plant designated G4111-4 (non-patented in the United States) which exhibits semi-double red florets with medium green foliage. The male parent (i.e., pollen parent) was the 'Laura' cultivar (U.S. Plant Pat. No. 7,087) which exhibits semi-double lavender florets with medium green foliage. The parentage of the new 'BFP-825 Salmon Rose' cultivar can be summarized as follows:

G4111-4x'Laura'.

The 'BFP-825 Salmon Rose' cultivar was discovered and selected during 1992 as a highly distinctive flowering plant from among the progeny of the stated cross at Arroyo Grande, Calif., U.S.A. This plant was initially designated BFP-825.

It was found that the new cultivar of the present invention:

(a) exhibits attractive semi-double light rose florets, (b) forms medium green foliage with zonation, and (c) exhibits a medium self-branching growth habit in the absence of a growth regulator.

When plant material of the 'BFP-825 Salmon Rose' cultivar is subjected to standard random amplified polymorphic DNA marker analysis (RAPD) using polymerase chain reaction (PCR) and a known set of DNA primers, it is found to exhibit a distinctive fingerprint map which is on file at the Ball FloraPlant Division of Geo. J. Ball, Inc. at Arroyo Grande, Calif., U.S.A.

The first act of asexual reproduction of the 'BFP-825 Salmon Rose' cultivar was accomplished when vegetative cuttings were taken from the initial selection in a controlled environment at Arroyo Grande, Calif., U.S.A., by a technician working under the direction and supervision of the originator of the new cultivar. Horticultural examination of plants resulting from such asexual propagation during 1993 has demonstrated that the combination of unique characteristics as herein described for the 'BFP-285 Salmon Rose' cultivar is firmly fixed and is retained through successive generations of such asexual reproduction.

The new 'BFP-825 Salmon Rose' cultivar has not been observed under all possible environmental conditions. Accordingly, the described phenotype may vary somewhat with variations in the environment, such as temperature, light intensity, and day length.

Of the many commercial cultivars, the 'Americana Cherry Rose' cultivar (U.S. Plant Pat. No. 7,935) is considered to be the most similar to the new cultivar of the present invention. When the new cultivar of the present invention is compared to the 'Americana Cherry Rose' cultivar, it is found that the 'BFP-825 Salmon Rose' cultivar exhibits distinctly larger umbels (e.g., approximately 11.0 to 13.0 cm. vs. approximately 9.4 to 11.0 cm.) and larger florets (e.g., approximately 4.6 to 5.2cm. vs. approximately 4.0 to 4.5 cm.).

The new cultivar of the present invention is being marketed by Geo. J. Ball, Inc. under the Designer trademark.

BRIEF DESCRIPTION OF THE PHOTOGRAPH

The accompanying photograph of FIG. 1 shows a typical plant of the new 'BFP-825 Salmon Rose' cultivar with colors being as nearly true as it is reasonably possible to make the same in color illustrations of this character. Typical flower and foliage characteristics are illuustrated. The plant was being grown in a greenhouse at West Chicago, Ill., U.S.A.

DETAILED DESCRIPTION

Figure 1:
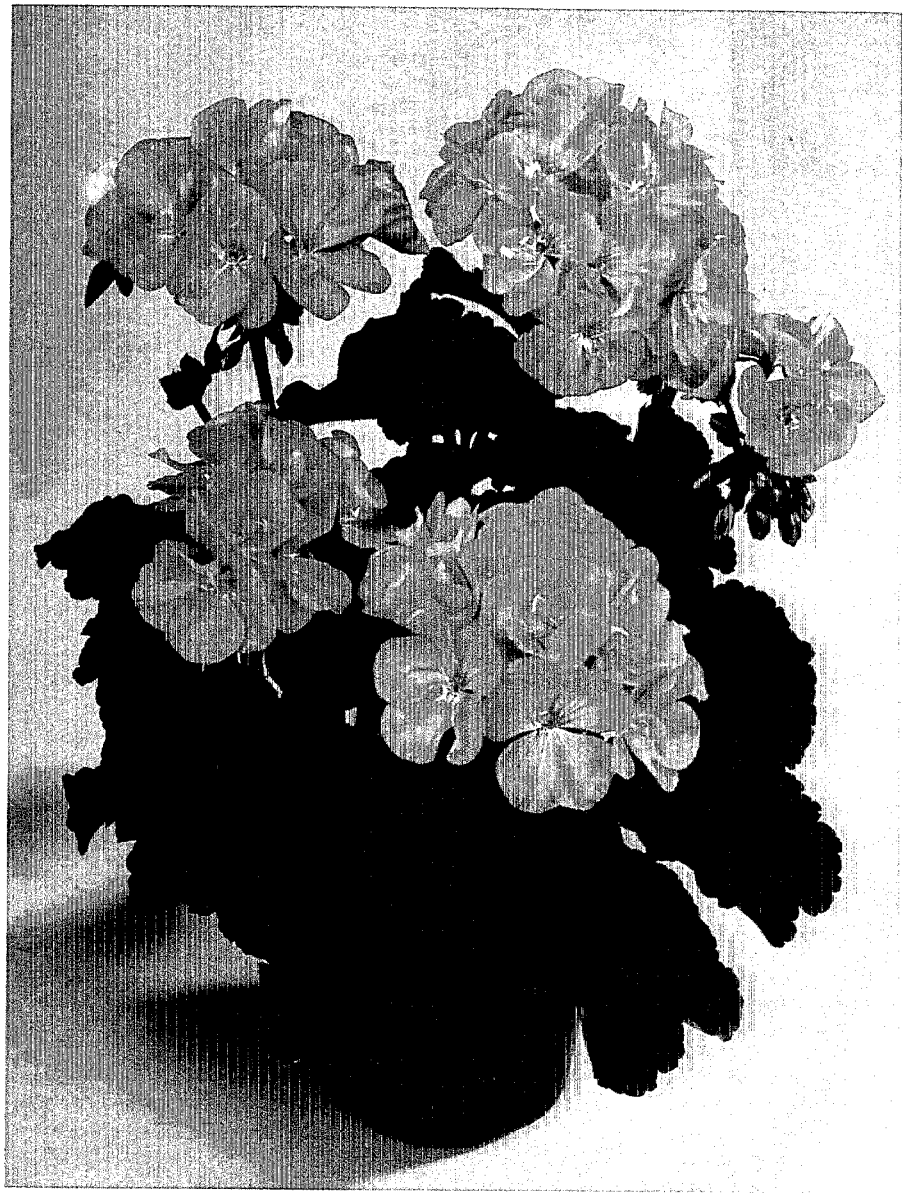

The following observations, measurements and comparisons describe plants grown in Ball FloraPlant's greenhouses located at West Chicago, Ill., U.S.A., under conditions which approximate those generally used in commercial practice. In the following description, color references are made to the R.H.S. Colour Chart of The Royal Horticultural Society, London, England. The color values were determined between 9:00 and 9:30 a.m. on Dec. 27, 1994, under natural light conditions of 2,000 footcandles.

Classification:

*Botanical.*—*Pelargonium×hortorum* Bailey, cv. 'BFP-825 Salmon Rose'.

*Commercial.*—Zonal Geranium.

INFLORESCENCE

A. Umbel:

*Average diameter.*—Approximately 11.0 to 13.0 cm. compared to approximately 9.4 to 11.0 cm. for the 'Americana Cherry Rose' cultivar.

*Average depth.*—Approximately 6.5 to 10.0 cm. compared to approximately 6.5 to 7.0 cm. for the 'Americana Cherry Rose' cultivar.

*Peduncle length.*—Approximately 14.0 to 20.0 cm. compared to approximately 13.5 to 24 cm. for the 'Americana Cherry Rose' cultivar.

*Pedicel length.*—Approximately 3.6 to 4.2 cm. compared to approximately 2.9 to 4.2 cm. for the 'Americana Cherry Rose' cultivar.

*Number of umbels/plant.*—When grown in a cm. pot at 9 weeks after the sticking of a rooted cutting, there commonly are approximately 3 to 4 umbels per plant. The 'Americana Cherry Rose' cultivar also commonly forms approximately 3 to 4 umbels per plant.

*Number of florets/umbel.*—When grown in 10 cm. pots at 9 weeks, approximately 27 to 34 florets per umbel commonly are formed. This compares to approximately 25 to 43 florets per umbel for the 'Americana Cherry Rose' cultivar under the same growing conditions.

B. Corolla:

*Average diameter.*—Approximately 4.6 to 5.2 cm. compared to approximately 4.0 to 4.5 cm. for the 'Americana Cherry Rose' cultivar.

*Form.*—Both the 'BFP-825 Salmon Rose' cultivar and the 'Americana Cherry Rose' cultivar are semi-double with petaloids. The 'BFP-825 Salmon Rose' cultivar commonly forms 5 to 6 petals per floret, and the 'Americana Cherry Rose' cultivar commonly forms 6 to 7 petals per floret.

*Number of petaloids.*—Commonly forms 2 to 3 petaloids per floret whereas the 'Americana Cherry Rose' cultivar commonly forms 2 to 5 petaloids per floret.

*Color.*—General tonality from a distance of three meters: Salmon. Adaxial: Red-Purple Group 57B. This compares to Red-Purple Group 57A for the 'Americana Cherry Rose' cultivar. Abaxial: Red-Purple Group 58C. This compares to Red-Purple Group 61C for the 'Americana Cherry Rose' cultivar C. Bud:

*Shape.*—Oval-rounded.

*Color.*—Adaxial: Red-Purple Group 57B compared to Red-Purple Group 57A for the 'Americana Cherry Rose' cuultivar. Abaxial: Red-Purple Group 58C compared to Red-Purple Group 61C for the 'Americana Cherry Rose' cultivar.

D. Reproductive organs:

*Androecium.*—The anthers are commonly approximately 1.5 to 2.0 mm. in length. The pollen color in Orange-Red Group 31A for both the 'BFP-825 Salmon Rose' cultivar and the 'Americana Cherry Rose' cultivar. The filaments are approximately 10 min. in length compared to approximately 12 mm. for the 'Americana Cherry Rose' cultivar.

*Gynoecium.*—The pistil length commonly is approximately 9 mm. There is a single stigma which commonly has a length of approximately 4 mm. which commonly branches into 5 parts, and the style length is approximately 5 mm.

*Fertility.*—Commonly does not produce fruits in the absence of mechanical fertilization.

E. Spring flowering response period: Approximately 6 to 7 weeks from rooted cuttings under standard greenhouse conditions.

F. Outdoor flower production: Freely flowering under outdoor growing conditions with substantially continuous blooming.

G. Durability: Ships well.

PLANT

A. Foliage: Medium green with zonation.

*Form.*—Reniform, with cordate base.

*Margin.*—Crenate.

*Color.*—Adaxial: Slightly lighter than Yellow-Green Group 147A with marginal zonation of Yellow-Green Group 147A for both the 'BFP-825 Salmon Rose' cultivar and the 'Americana Cherry Rose' cultivar. Abaxial: Yellow-Green Group 146A for both the 'BFP-825 Salmon Rose' cultivar and the 'Americana Cherry Rose' cultivar.

*Size.*—Approximately 7.7 to 11.5 cm. at the widest point and approximately 7.2 to 10.5 cm. at the narrowest point. This compares to approximately 9.0 to 10.0 cm. at the widest point and approximately 7.7 to 8.5 cm. at the narrowest point for the 'Americana Cherry Rose' cultivar.

B. General appearance and form:

*Internode length.*—Commonly varies from approximately 1.0 to 2.6 cm. This compares to approximately 1.2 to 1.9 cm. for the 'Americana Cherry Rose' cultivar.

*Branching pattern.*—Freely basal branching. No pinching is required to obtain self-branching. A medium self-branching growth habit is observed in the absence of a growth regulator.

*Height.*—Approximately 32 to 35 cm. above a 10 cm. pot at 9 weeks under standard greenhouse conditions. This compares at approximately 29 to 34 cm. for the 'Americana Cherry Rose' cultivar.

I claim:

1. A new and distinct Geranium plant named 'BFP-825 Salmon Rose', substantially as herein shown and described, which:

(a) exhibits attractive semi-double light rose florets, (b) forms medium green foliage with zonation, and (c) exhibits a medium self-branching growth habit in the absence of a growth regulator.

* * * * *